(12) United States Patent
Honsberger et al.

(10) Patent No.: US 8,899,540 B2
(45) Date of Patent: Dec. 2, 2014

(54) COUNTERBALANCE MECHANISM

(75) Inventors: Brent A. Honsberger, Sugar Grove, PA (US); Warren A. Waxham, Lexington, KY (US)

(73) Assignee: Weber Knapp Company, Jamestown, NY (US)

( * ) Notice: Subject to any disclaimer, the term of this patent is extended or adjusted under 35 U.S.C. 154(b) by 786 days.

(21) Appl. No.: 13/017,443

(22) Filed: Jan. 31, 2011

(65) Prior Publication Data

US 2012/0192382 A1 Aug. 2, 2012

(51) Int. Cl.
*A47F 5/00* (2006.01)
*F16M 11/00* (2006.01)
*F16M 13/00* (2006.01)
*E05F 1/10* (2006.01)
*A61N 5/06* (2006.01)

(52) U.S. Cl.
CPC ............. *E05F 1/1075* (2013.01); *A61N 5/0614* (2013.01); *A61N 2005/0633* (2013.01); *E05Y 2201/488* (2013.01); *E05Y 2201/492* (2013.01); *E05Y 2201/702* (2013.01); *E05Y 2600/20* (2013.01); *E05Y 2800/21* (2013.01)
USPC ............ 248/281.11; 248/280.11; 248/292.11; 248/292.14; 248/123.11; 267/174; 267/178

(58) Field of Classification Search
USPC ............. 248/280.11, 281.11, 292.14, 123.11, 248/123.2; 267/73, 150, 174, 178
See application file for complete search history.

(56) References Cited

U.S. PATENT DOCUMENTS

| | | | |
|---|---|---|---|
| 2,131,693 A | | 9/1938 | Smith |
| 2,709,057 A | * | 5/1955 | Gould ........................... 248/543 |
| 3,426,190 A | | 2/1969 | Bobrick |
| 4,360,180 A | | 11/1982 | Bruneau |
| 4,447,031 A | | 5/1984 | Souder, Jr. et al. |
| 4,559,879 A | | 12/1985 | Hausser |
| 4,747,353 A | | 5/1988 | Watt |
| 4,981,085 A | | 1/1991 | Watt |
| 5,180,136 A | | 1/1993 | Sova |
| 5,181,620 A | | 1/1993 | Watt |
| 5,213,293 A | * | 5/1993 | Muentener et al. ...... 248/123.11 |
| 5,402,690 A | * | 4/1995 | Sekiguchi et al. ......... 74/490.01 |
| 5,797,331 A | | 8/1998 | Watt |

(Continued)

*Primary Examiner* — Terrell McKinnon
*Assistant Examiner* — Michael McDuffie
(74) *Attorney, Agent, or Firm* — Simpson & Simpson, PLLC

(57) ABSTRACT

A counterbalance mechanism including: a housing having a first aligned pair of through holes and a second aligned pair of through holes; a pivot nose having a third aligned pair of through holes, a fourth aligned pair of through holes and an aligned pair of arcuate slots; an energy storage device having first and second spring mounts and at least one spring, the first spring mount having at least one first flange and a pivot flange having a fifth through hole, the second spring mount having at least one second flange and a sixth through hole and the at least one spring includes first and second ends, the first end is secured to the at least one first flange and the second end is secured to the at least one second flange; a first pivot pin disposed in the first aligned pair of through holes and the third aligned pair of through holes; a stop member disposed in the second aligned pair of through holes and the aligned pair of arcuate slots; a second pivot pin disposed in the fourth aligned pair of through holes and the fifth through hole; a force magnitude adjuster arranged to control a force of the at least one spring; and, a force angle adjuster arranged to control a force direction of the at least one spring.

9 Claims, 15 Drawing Sheets

(56) References Cited

U.S. PATENT DOCUMENTS

| | | | |
|---|---|---|---|
| 6,030,130 A * | 2/2000 | Paddock et al. | 396/421 |
| 6,375,175 B1 * | 4/2002 | Baumann et al. | 267/172 |
| 6,397,988 B1 * | 6/2002 | Ptak | 188/380 |
| 6,732,988 B2 * | 5/2004 | Ihalainen et al. | 248/276.1 |
| 7,255,311 B2 * | 8/2007 | Metelski | 248/123.11 |
| 7,412,776 B2 * | 8/2008 | Iikubo et al. | 33/503 |
| 7,562,851 B2 * | 7/2009 | Hein et al. | 248/281.11 |
| 8,066,251 B2 * | 11/2011 | Brown | 248/584 |
| 8,152,126 B2 * | 4/2012 | Hardtke | 248/584 |
| 8,689,646 B2 * | 4/2014 | Carr | 73/862.61 |
| 2004/0245419 A1 * | 12/2004 | Sweere et al. | 248/276.1 |
| 2006/0102819 A1 * | 5/2006 | Li | 248/280.11 |
| 2007/0080275 A1 * | 4/2007 | Stachowski et al. | 248/323 |
| 2010/0019112 A1 * | 1/2010 | Chi | 248/281.11 |
| 2010/0155558 A1 * | 6/2010 | Zhang et al. | 248/281.11 |

* cited by examiner

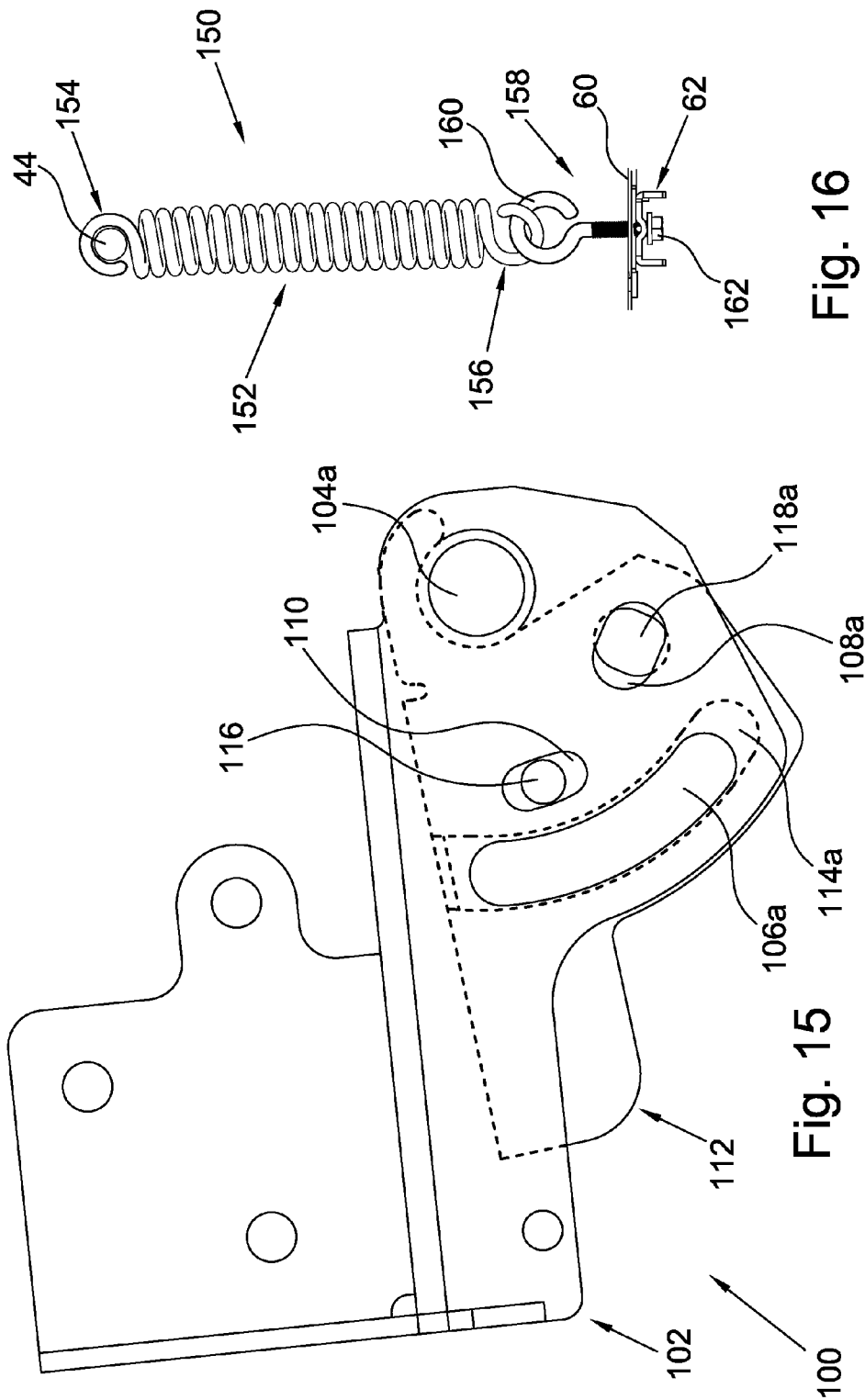

COUNTERBALANCE MECHANISM

FIELD OF THE INVENTION

The invention broadly relates to counterbalances, more specifically to adjustable counterbalances, and even more particularly to an adjustable counterbalance including force magnitude adjustment and force angle or direction adjustment.

BACKGROUND OF THE INVENTION

Counterbalance mechanisms including a pair of interconnected parallelograms linkages, which are provided with counterbalance springs, are well known, as disclosed in U.S. Pat. Nos. 2,131,693; 3,426,190; 4,447,031; and, 5,180,136, which patents are incorporated by reference in their entireties herein. Counterbalance mechanisms having individually adjustable counterbalance springs are also known in the art, as shown in U.S. Pat. No. 4,447,031. It is also known to provide a mechanism for controlling vertical movement of a surface, such as a desk, a table top or a shelf relative to a supporting base wherein a counterbalance mechanism is provided to balance at least part of the weight of the surface and/or weight supported thereon and a brake mechanism is provided to releasably retain the surface in a desired vertical position, as taught in U.S. Pat. Nos. 4,130,069; 4,360,180; 4,559,879; 4,747,353; 4,981,085; 5,181,620; and, 5,797,331, which patents are incorporated by reference in their entireties herein. Moreover, a counterbalance mechanism employing a pivotally supported member coupled via cables to a surface to be supported for vertical movement and a spring for controlling pivotal movement of the member are taught in U.S. Pat. Nos. 5,181,620 and 5,797,331.

Devices having heavy and/or large moveable covers or enclosures regularly require a means for controlling the movement of the cover. Such covers and enclosures often are repeatedly manipulated from one position to another, e.g., open and closed positions, or moved through a range of motion, e.g., 10-60 degrees. As this movement must be performed by a user of the device, such as a person and not a powered machine, assistance must be provided to the user in order to facilitate and control the movement. If the foregoing assistance is not provided, the cover or enclosure may be difficult if not impossible to move, or in the alternative, a situation may exist where the user can not control the movement of the cover thereby resulting in damage to the cover.

A tanning bed is an example of such a device. Production variations in these devices cause variability in the location of the center of gravity of the tanning bed lid. Moreover, the size and nature of the tanning bed lids may require that the lids be rotatably connected at each end so that the lid moves evenly.

As can be derived from the variety of devices and methods directed at providing counterbalancing forces for an enclosure cover, many means have been contemplated to accomplish the desired end, i.e., consistent, balanced and controlled forces to the cover. Heretofore, tradeoffs between expense, complexity and performance were required.

BRIEF SUMMARY OF THE INVENTION

Broadly, the present invention includes a means for providing a uniform counterbalancing force across a variety of enclosure covers and lids. The present invention accommodates for production variations in the center of gravity locations of the cover/lid assemblies as well as balancing opposite ends of covers/lids which require discreet counterbalance devices at each respective end. The present invention includes adjustment of force magnitude as well as independent adjustment of the force angle of the energy storage device. Having such an arrangement, the present invention provides means for moving a very heavy cover/lid, e.g., 250-350 pounds (lbs), through its entire range of angular motion with minimal friction while maintaining very low operating forces, e.g., 5-10 lbs.

The present invention broadly comprises a counterbalance mechanism including a housing having a first aligned pair of through holes and a second aligned pair of through holes and a pivot nose having a third aligned pair of through holes, a fourth aligned pair of through holes and an aligned pair of arcuate slots. The counterbalance further includes an energy storage device having first and second spring mounts and at least one spring, the first spring mount having at least one first flange and a pivot flange having a fifth through hole, the second spring mount having at least one second flange and a sixth through hole and the at least one spring includes first and second ends, the first end is secured to the at least one first flange and the second end is secured to the at least one second flange. Moreover, the counterbalance further includes a first pivot pin disposed in the first aligned pair of through holes and the third aligned pair of through holes, a stop member disposed in the second aligned pair of through holes and the aligned pair of arcuate slots and a second pivot pin disposed in the fourth aligned pair of through holes and the fifth through hole. Still yet further, the counterbalance includes a force magnitude adjuster arranged to control a force of the at least one spring and a force angle adjuster arranged to control a force direction of the at least one spring.

In some embodiments, the housing includes a seventh through hole and the force angle adjuster is arranged to pass through the seventh through hole. In some embodiments, the fourth aligned pair of through holes are keyed through holes. In some embodiments, the first spring mount includes a pair of oppositely disposed first flanges arranged symmetrically about the pivot flange, the second spring mount includes a pair of oppositely disposed second flanges arranged symmetrically about the sixth through hole and two springs each including first and second ends, each of the first ends is secured to one of the pair of first flanges and each of the second ends is secured to one of the pair of second flanges. In some embodiments, the force magnitude adjuster controls the force of the at least one spring by altering a length of the at least one spring. In some embodiments, the force angle adjuster controls the force direction by altering a position of the second spring mount relative to the fifth through hole. In some embodiments, the stop member is a third pivot pin. In some embodiments, when the first pivot pin, the second pivot pin and the force direction are in aligned registration substantially no torque is applied to the pivot nose.

In a further embodiment, the present invention counterbalance mechanism includes a force magnitude adjuster arranged to control a force of an energy storage device and a force angle adjuster arranged to control a force direction of the energy storage device. In some embodiments, the counterbalance mechanism further includes a housing having a first through hole and a second through hole, a pivot nose having a third through hole, a fourth through hole and an arcuate slot, an energy storage device, a first pivot pin disposed in the first through hole and the third through hole, and a second pivot pin disposed in the fourth through hole and the energy storage device. In some embodiments, the counterbalance mechanism further includes a housing having a first aligned pair of through holes and a second aligned pair of through holes, a pivot nose having a third aligned pair of through holes, a fourth aligned pair of through holes and an aligned pair of arcuate slots, an energy storage device, a first pivot pin disposed in the first aligned pair of through holes and the third aligned pair of through holes, and a second pivot pin disposed in the fourth aligned pair of through holes and the energy storage device. In some embodiments, the counterbalance mechanism further includes a housing having a first through hole and a second through hole, a pivot nose having a third through hole, a first arcuate slot, a second arcuate slot and a third arcuate slot, an adjustment plate rotatably secured to the pivot nose, and the adjustment plate arranged to rotate about the third through hole, the adjustment plate having a fourth arcuate slot, a fifth through hole and a sixth through hole, wherein the fourth arcuate slot is arranged adjacent to the first arcuate slot, the fifth through hole is arranged adjacent to the third arcuate slot and the sixth through hole are adjacent to the second arcuate slot. These embodiments further include an energy storage device, a first pivot pin disposed in the first through hole and the third through hole, and a second pivot pin disposed in the sixth through hole and the energy storage device, wherein the force angle adjuster comprises the pivot nose and the adjustment plate and rotating the adjustment plate relative to the pivot nose changes a force direction of the energy storage device. In some embodiments, the counterbalance mechanism further includes a housing having a first aligned pair of through holes and a second aligned pair of through holes, a pivot nose having a third aligned pair of through holes, a first aligned pair of arcuate slots, a second aligned pair of arcuate slots and a third arcuate slot, and an adjustment plate rotatably secured to the pivot nose, the adjustment plate arranged to rotate about the third aligned pair of through holes, the adjustment plate having a fourth arcuate slot, a fifth through hole and a sixth aligned pair of through holes, wherein the fourth arcuate slot is arranged adjacent to the first aligned pair of arcuate slots, the fifth through hole is arranged adjacent to the third arcuate slot and the sixth aligned pair of through holes are adjacent to the second aligned pair of arcuate slots. These embodiments further include an energy storage device, a first pivot pin disposed in the first aligned pair of through holes and the third aligned pair of through holes, and a second pivot pin disposed in the sixth aligned pair of through holes and the energy storage device, wherein the force angle adjuster comprises the pivot nose and the adjustment plate and rotating the adjustment plate relative to the pivot nose changes a force direction of the energy storage device.

In a further embodiment, the present invention counterbalance mechanism includes a housing including a first aligned pair of through holes and a second aligned pair of through holes and a pivot nose including a third aligned pair of through holes, a first aligned pair of arcuate slots, a second aligned pair of arcuate slots and a third arcuate slot. The counterbalance further includes an adjustment plate rotatably secured to the pivot nose, the adjustment plate arranged to rotate about the third aligned pair of through holes, the adjustment plate including a fourth arcuate slot, a fifth through hole and a sixth aligned pair of through holes, wherein the fourth arcuate slot is arranged adjacent to the first aligned pair of arcuate slots, the fifth through hole is arranged adjacent to the third arcuate slot and the sixth aligned pair of through holes are adjacent to the second aligned pair of arcuate slots. The counterbalance further includes an energy storage device including first and second spring mounts and at least one spring, the first spring mount including at least one first flange and a pivot flange having a seventh through hole, the second spring mount including at least one second flange and an eighth through hole and the at least one spring includes first and second ends, the first end is secured to the at least one first flange and the second end is secured to the at least one second flange. The counterbalance further includes a first pivot pin disposed in the first aligned pair of through holes and the third aligned pair of through holes, a stop member disposed in the second aligned pair of through holes, the first aligned pair of arcuate slots and the fourth arcuate slot and a second pivot pin disposed in the sixth aligned pair of through holes and the seventh through hole. The counterbalance further includes a force magnitude adjuster arranged to control a force of the at least one spring. When the adjustment plate is rotated relative to the pivot nose, a force direction of the at least one spring is changed.

In some embodiments, the first spring mount includes a pair of oppositely disposed first flanges arranged symmetrically about the pivot flange, the second spring mount includes a pair of oppositely disposed second flanges arranged symmetrically about the eighth through hole and two springs each including first and second ends, each of the first ends is secured to one of the pair of first flanges and each of the second ends is secured to one of the pair of second flanges. In some embodiments, the force magnitude adjuster controls the force of the at least one spring by altering a length of the at least one spring. In some embodiments, the stop member is a third pivot pin. In some embodiments, when the first pivot pin, the second pivot pin and the force direction are in aligned registration substantially no torque is applied to the pivot nose.

In yet a further embodiment, the present invention counterbalance mechanism includes a housing including a first aligned pair of through holes, a pivot nose including a second aligned pair of through holes and a third aligned pair of through holes, an energy storage device, a first pivot pin disposed in the first aligned pair of through holes and the second aligned pair of through holes, a second pivot pin disposed in the third aligned pair of through holes and the energy storage device, a force magnitude adjuster arranged to control a force of the energy storage device, and a force angle adjuster arranged to control a force direction of the energy storage device.

In still yet a further embodiment, the present invention counterbalance mechanism includes a housing including a first through hole, a pivot nose including a second through hole and a third through hole, an energy storage device, a first pivot pin disposed in the first through hole and the second through hole, a second pivot pin disposed in the third through hole and the energy storage device, a force magnitude adjuster arranged to control a force of the energy storage device, and a force angle adjuster arranged to control a force direction of the energy storage device.

It is a general object of the present invention to provide a counterbalance mechanism including both energy storage device force adjustment and a modifiable zero torque rotational position.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention taken with the accompanying drawing figures, in which:

FIG. 15 is a side elevational view of yet another embodiment of a pivot nose used in a present invention counterbalance mechanism; and, FIG. 16 is a side elevational view of another embodiment of an energy storage device assembly for use in an embodiment of a present invention counterbalance mechanism.

DETAILED DESCRIPTION OF THE INVENTION

Figure 1:
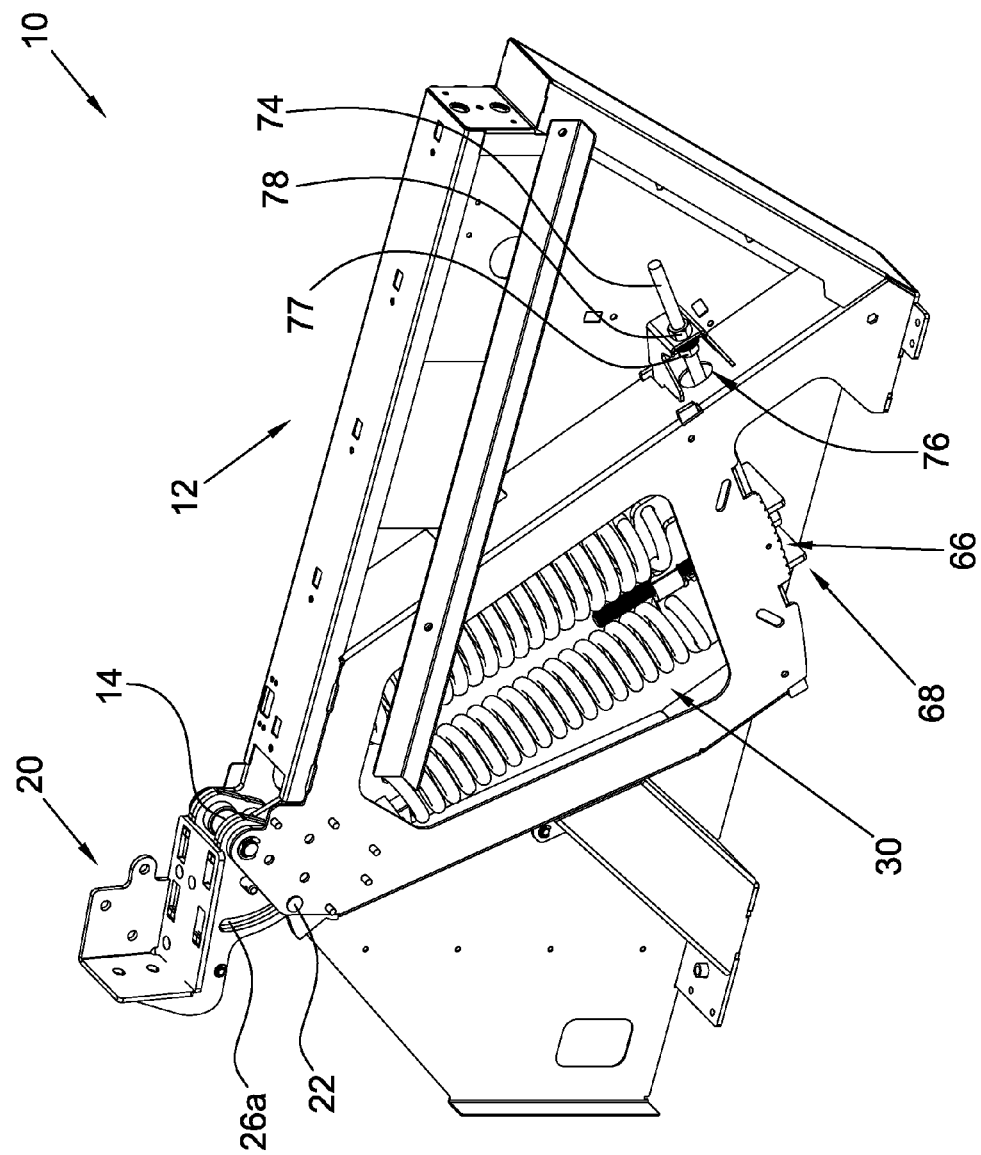
FIG. 1 is a perspective view of an embodiment of a present invention counterbalance mechanism.
Figure 2:
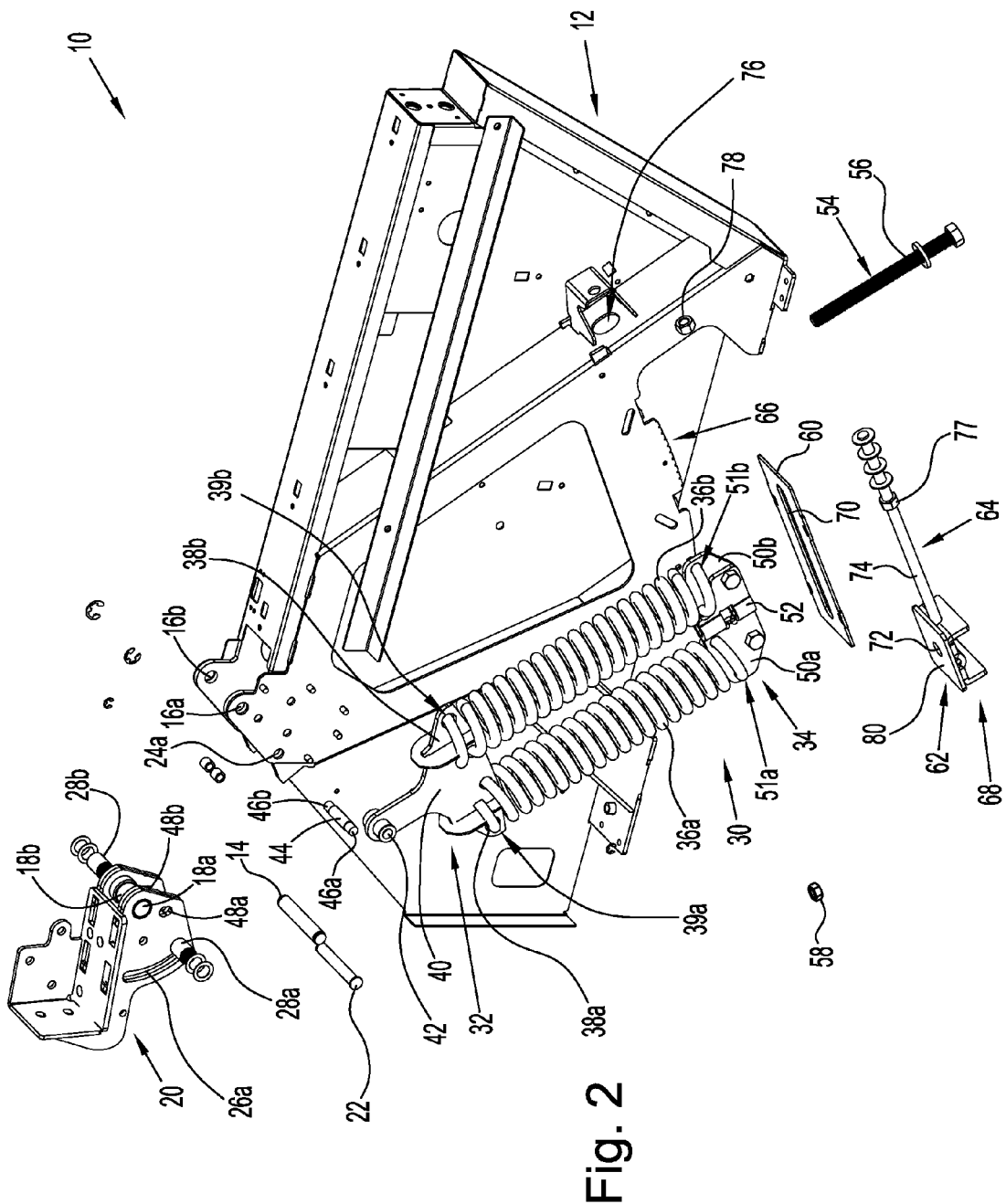
FIG. 2 is an exploded perspective view of the embodiment of the present invention counterbalance mechanism of FIG. 1.
Figure 3:
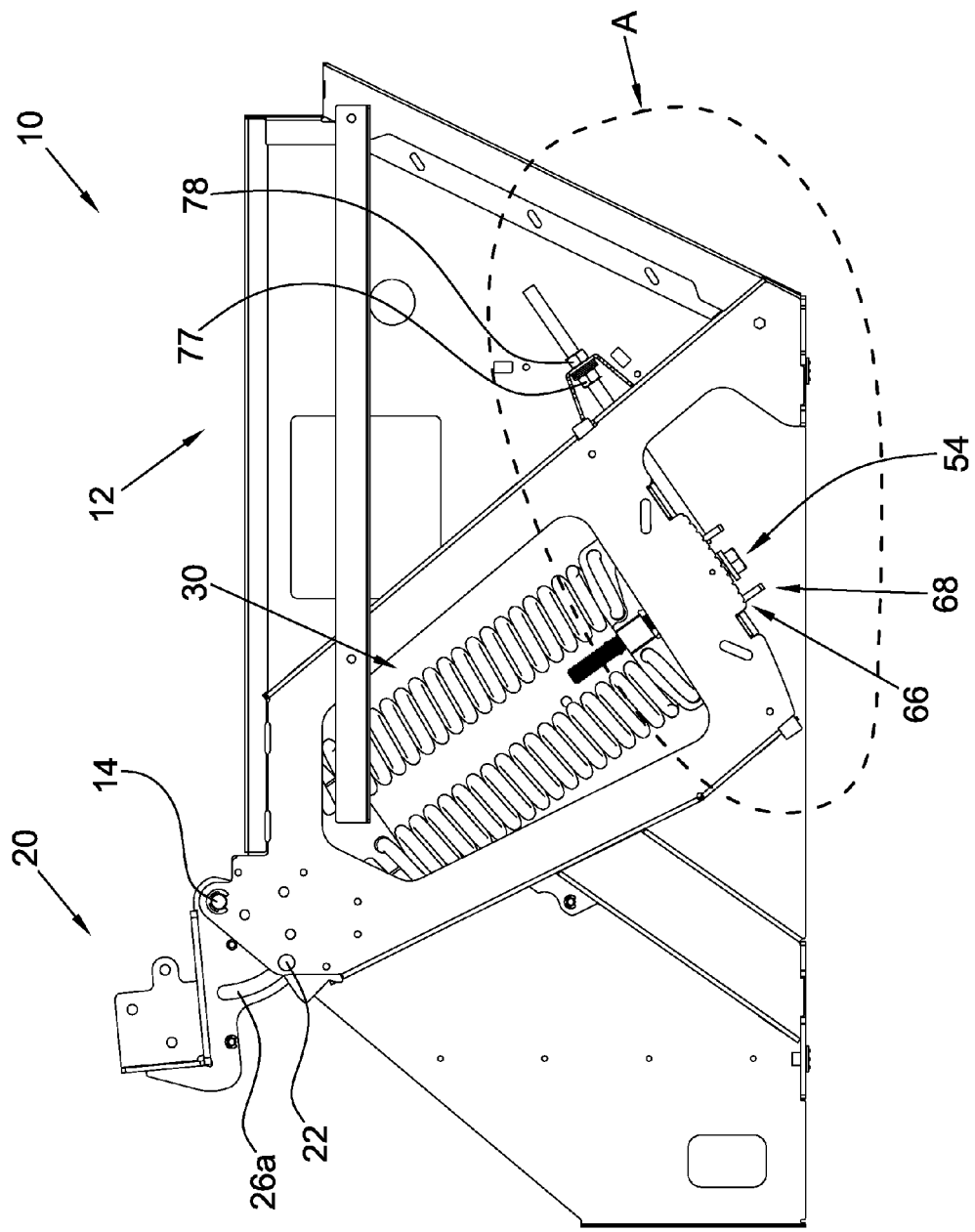
FIG. 3 is a side elevational view of the embodiment of the present invention counterbalance mechanism of FIG. 1.
Figure 4:
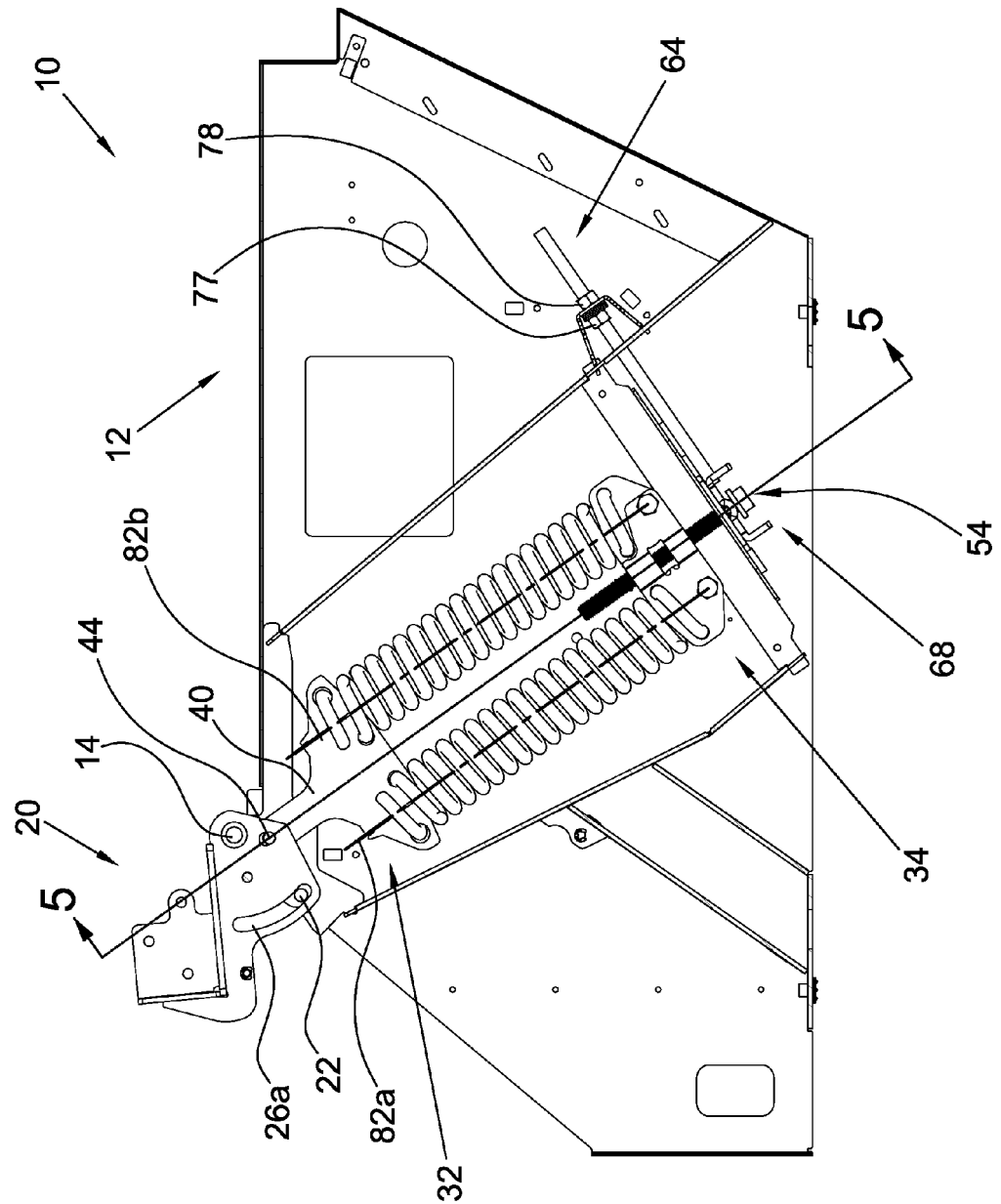
FIG. 4 is a side elevational view of the embodiment of the present invention counterbalance mechanism of FIG. 1 having side walls removed to expose the inner components.
Figure 5:
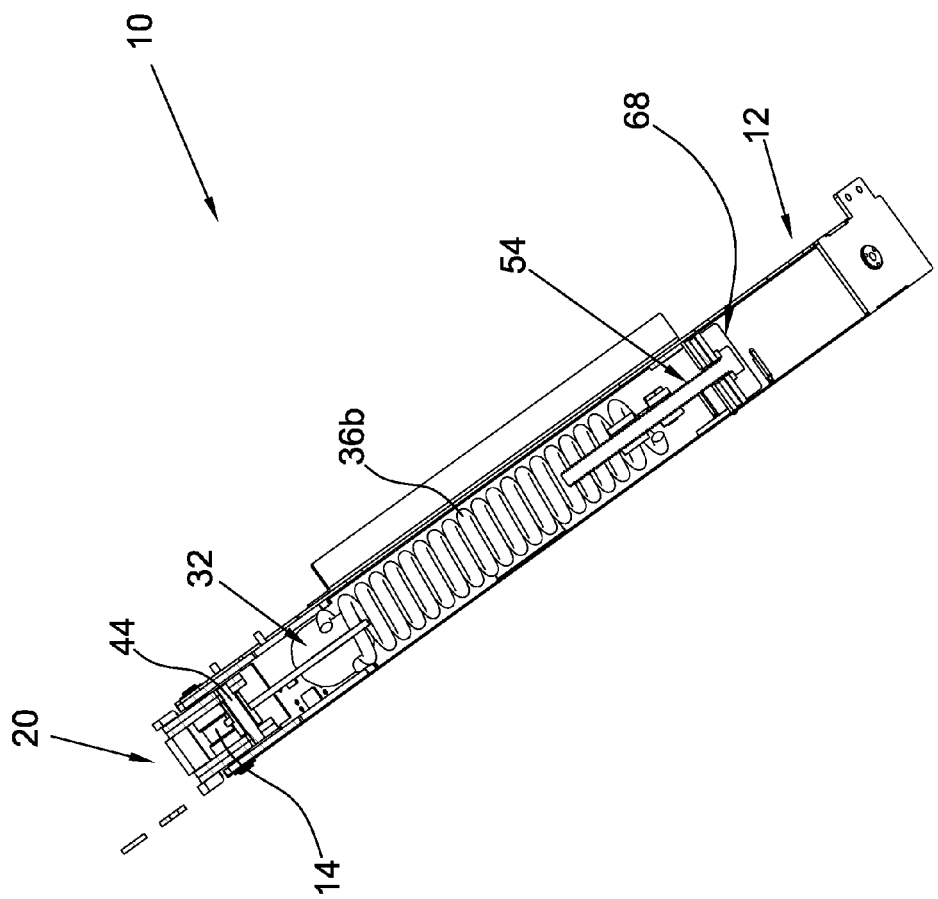
FIG. 5 is a cross-sectional view of the embodiment of the present invention counterbalance mechanism of FIG. 4 taken generally along line 5-5.
Figure 6:
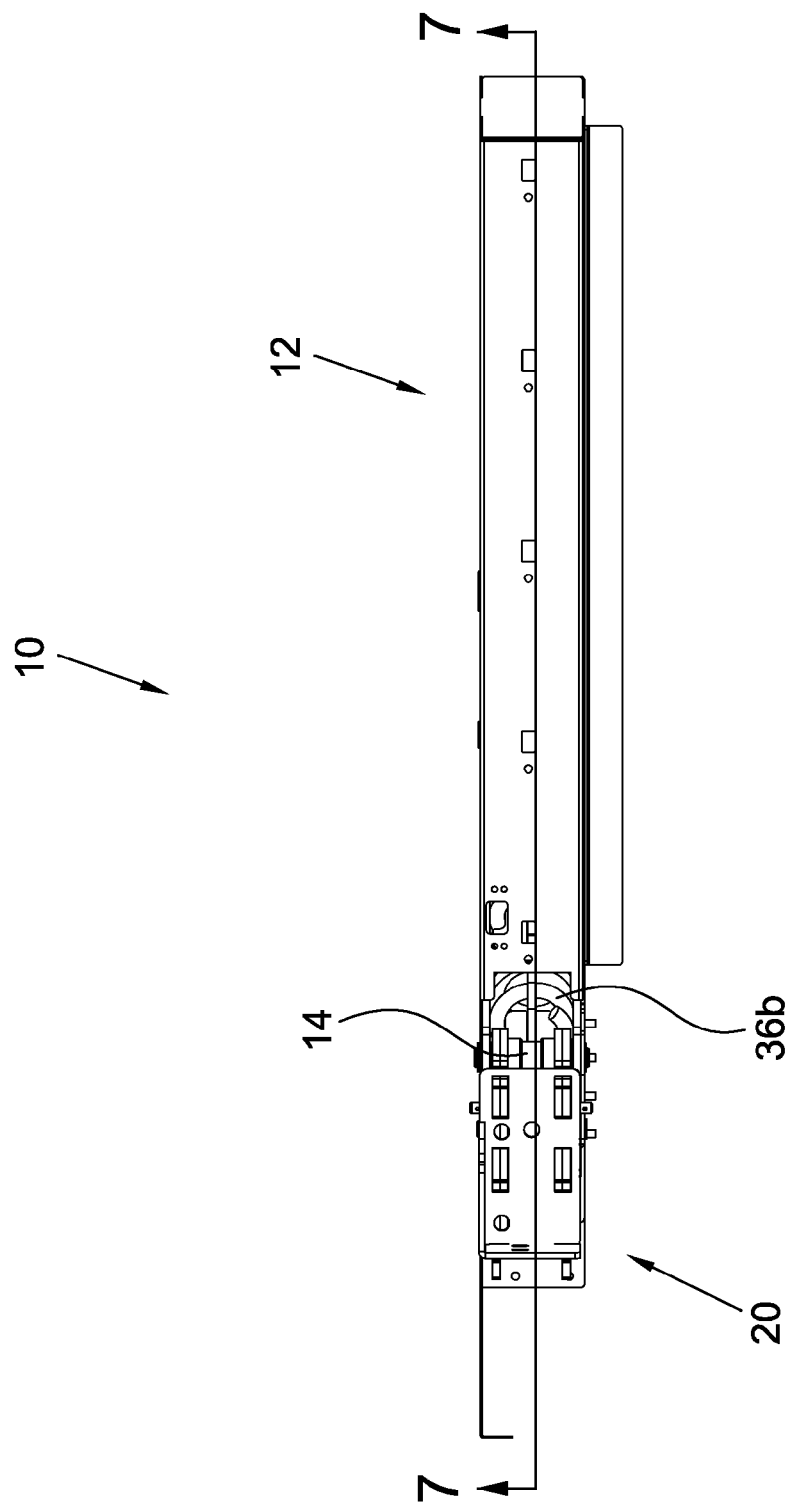
FIG. 6 is a top plan view of the embodiment of the present invention counterbalance mechanism of FIG. 1.
Figure 7:
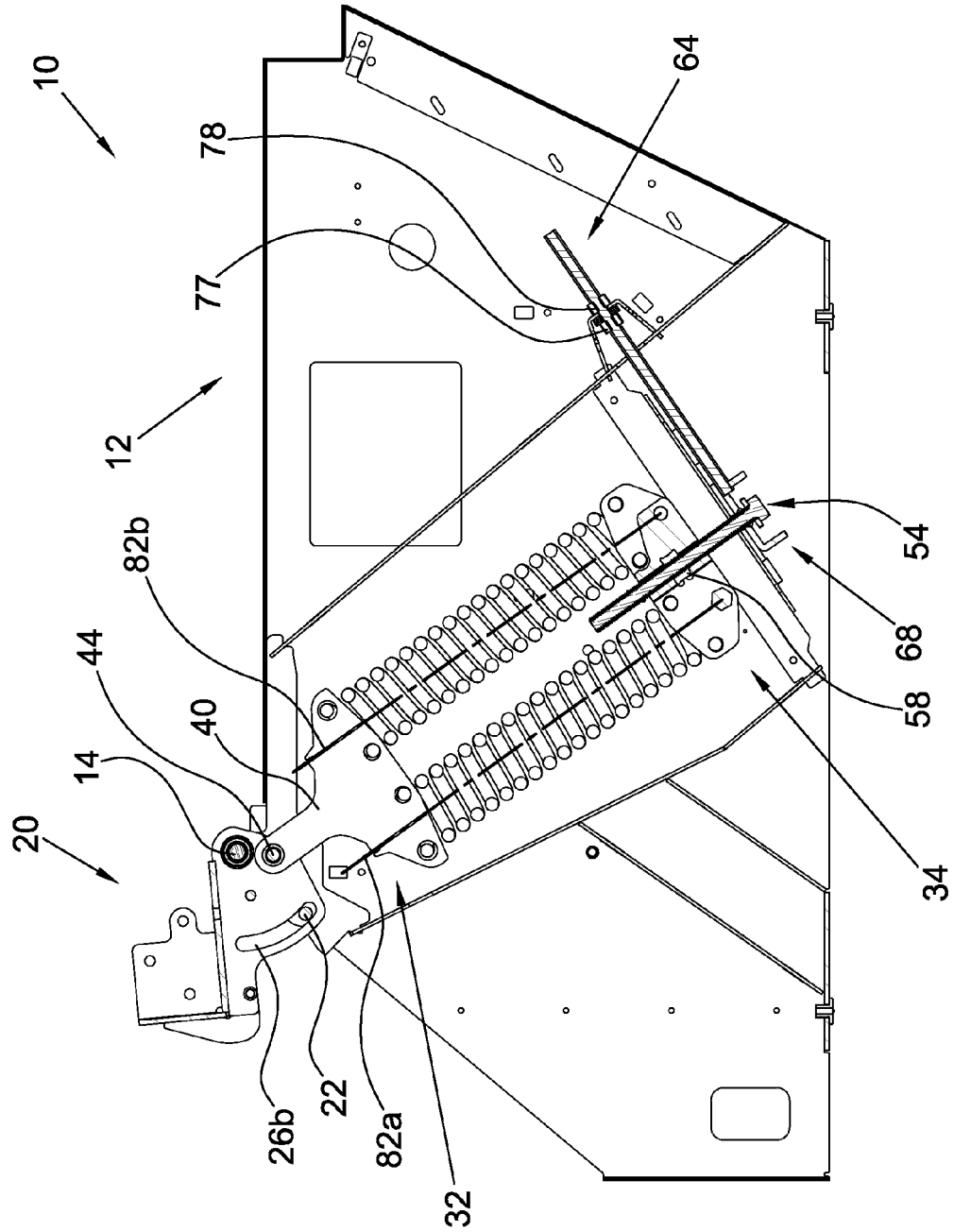
FIG. 7 is a cross-sectional view of the embodiment of the present invention counterbalance mechanism of FIG. 6 taken generally along line 7-7.
Figure 8:
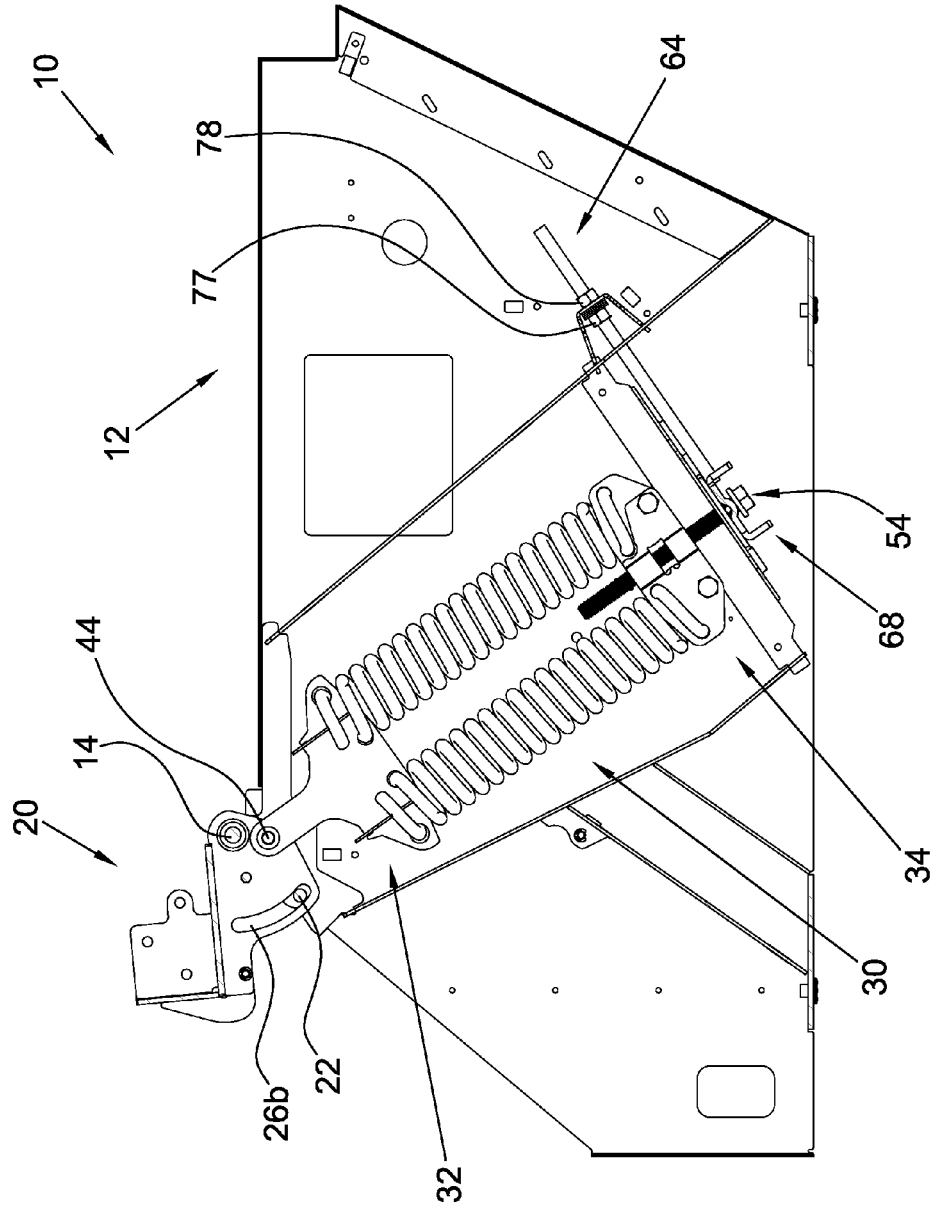
FIG. 8 is a side elevational view of the embodiment of the present invention counterbalance mechanism of FIG. 1 having side walls removed to expose the inner components and having the pivot slider positioned in a middle position.

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. As used herein, "aligned pair" is intended to mean oppositely disposed complimentary structures, e.g., an aligned pair of through holes are positioned such that a cylindrical rod may pass through each hole simultaneously, or in other words, the axes defining the through holes are coincident with the axis of the cylindrical rod. As used herein, "energy storage device" is intended to mean any device capable of storing mechanical energy, including but not limited to a pressure cylinder, a torsion spring, an extension spring, a compression spring and a leaf spring. Although any methods, devices or materials similar or equivalent to those described herein can be used in the practice or testing of the invention, the preferred methods, devices, and materials are now described.

It has been recognized that in some cover arrangements, e.g., a tanning bed cover, the dual attachment, or attachment of the cover at each respective end, creates the need for balancing the angles of each end of the lid as well as the forces applied to each end. The present invention provides a convenient and effective means of performing such complex balancing. However, it should be appreciated that based on the type of use of the present invention counterbalance mechanism, one counterbalance mechanism may be used at one end of the cover/lid or alternately may be arranged at the middle of the cover/lid. Additionally, more than one counterbalance mechanism may be used, for example, three counterbalance mechanisms arranged equidistantly along a cover/lid. Such variations are within the spirit and scope of the claimed invention.

Although the embodiments described herein comprise an energy storage device which is a spring assembly, any suitable energy storage device may be used, and such variations are within the spirit and scope of the claimed invention. Moreover, although the embodiments depicted herein comprise a housing weldment and a pivot nose weldment, other housing and pivot nose structures may also be used, e.g., stamped, cast or molded structures, and such variations are within the spirit and scope of the claimed invention. Furthermore, although the embodiments depicted in the figures show symmetrical components which each comprise aligned pairs of through holes and arcuate slots, the present invention also includes embodiments having discreet through holes and arcuate slots, i.e., not forming an aligned pair. For example, lower torque applications are suited to embodiments having all components mounted to and interacting with one side of a housing, thereby eliminating the need for complimentary through holes and arcuate slots on the opposite side of the housing. Such variations are within the spirit and scope of the claimed invention.

An embodiment of the present invention is shown in the figures. Counterbalance device 10 comprises main housing 12 which forms a central mounting structure for most other components. Pivot pin 14 is disposed within openings 16a and 16b of housing 12 and openings 18a and 18b of pivot nose 20 thereby pivotably securing pivot nose 20 within housing 12. Travel limit pin 22 is disposed within opening 24a and 24b (not shown) of housing 12 and arcuate slots 26a and 26b of pivot nose 20 thereby limiting the pivoting movement of pivot nose 20, i.e., pivot nose 20 may pivot to the extent permitted by the length of arcuate slots 26a and 26b. It should be appreciated that travel limit pin 22 acts as a stop member for the rotation of pivot nose 20, and that other stop members may also be used, e.g., protrusions extending from housing 12 into arcuate slots 26a and 26b. Such variations in the type of stop member fall within the spirit and scope of the claimed invention. In some embodiments, the pivoting movement of pivot nose 20 is further facilitated by including bearings 28a and 28b within openings 18a and 18b, i.e., arranged between openings 18a and 18b and pivot pin 14. Moreover, a lubricant may also be provided along the length of pivot pin 14 to further facilitate pivoting movement. An example of such a lubricant includes Nevastane® Lube sold by Total Lubricants USA, Inc.

The embodiment of the present invention depicted as counterbalance device 10 further comprises energy storage device 30. Energy storage device 30 comprises first spring mount 32, second spring mount 34 and springs 36a and 36b arranged therebetween. First spring mount 32 comprises oppositely disposed flanges 38a and 38b where first ends 39a and 39b of springs 36a and 36b are releasably secured. First spring mount 32 further comprises mounting flange 40 arranged between flanges 38a and 38b and extending therefrom. Mounting flange 40 comprises through hole 42 wherein spring load pin 44 is disposed. It should be appreciate that the location of through hole 42 or the equivalent thereof, corresponds to the location of the pivot axis of the energy storage device. Ends 46a and 46b are further disposed within openings 48a and 48b of pivot nose 20. It should be appreciated that openings 48a and 48b are keyed such that load pin 44 may be passed through the larger portions of openings 48a and 48b during assembly, while load pin 44 is disposed in the smaller portions of openings 48a and 48b after assembly, e.g., during use. Additionally, a lubricant may also be provided along the length of load pin 44 or within through hole 42 to further facilitate pivoting movement. An example of such a lubricant includes Nevastane® Lube. Second spring mount 34 comprises oppositely disposed flanges 50a and 50b where second ends 51a and 51b of springs 36a and 36b are releasably secured. Second spring mount 34 further comprises through hole 52 arranged between flanges 50a and 50b wherein force magnitude adjuster 54 is adjustably disposed. In the embodiment shown in the figures, force magnitude adjuster 54 is depicted as a tensioner comprising bolt 56 and nut 58. The movement of force magnitude adjuster 54 may be aided by an application of a lubricant such as Nevastane® Lube along the length bolt 56. As the relationship of the position of bolt 56 relative to nut 58 changes, the distance between first spring mount 32 and second spring mount 34 is shortened or lengthened, resulting in lesser or greater tension, i.e., force, applied by springs 36a and 36b, respectively. It should be appreciated that other methods of altering the force magnitude of the energy storage device may also be used, e.g., altering the winding of the springs, changing the number of active coils of the springs by fixedly securing adjacent coils, changing the number of active coils of the springs by rotating some of the end coils out of each respective mount and by changing the air pressure within the pressure cylinder (for embodiments comprising an energy storage device which is a pressure cylinder), and such variations are within the spirit and scope of the claims.

Counterbalance device 10 further comprises adjustment spanner plate 60, pivot slider 62 and pivot slider pin 64. Adjustment spanner plate 60 is arranged adjacent force angle adjustment scale 66. Pivot slider 62 and pivot slider pin 64 collectively form force angle assembly 68. Adjustment spanner plate 60 comprises slotted opening 70, while pivot slider 62 comprises through hole 72. Both slotted opening 70 and through hole 72 are in registered alignment with through hole 52. As such, force magnitude adjuster 54 is disposed within slotted opening 70, through hole 72 and through hole 52. The position of pivot slider 62, i.e., its position relative to force angle adjustment scale 66, is altered by adjusting pivot slider pin 64. For example, in the embodiments shown in the figures, pivot slider pin 64 is bolt 74 arranged to pass within through hole 76 of housing 12. It should be noted that although hole 76 is shown as part of housing 12, hole 76 may also be considered to be part of a bracket attached to housing 12, or any other structure external to housing 12. By altering the relationship of the positions of nuts 77 and 78 relative to bolt 74 moves the position of pivot slider 62 relative to housing 12 and thereby force angle adjustment scale 66. The movement of pivot slider 62 and pivot slider pin 64 may be aided by an application of a lubricant such as Nevastane® Lube along the length pivot slider pin 64 and/or on surface 80 of pivot slider 62.

Figure 9:
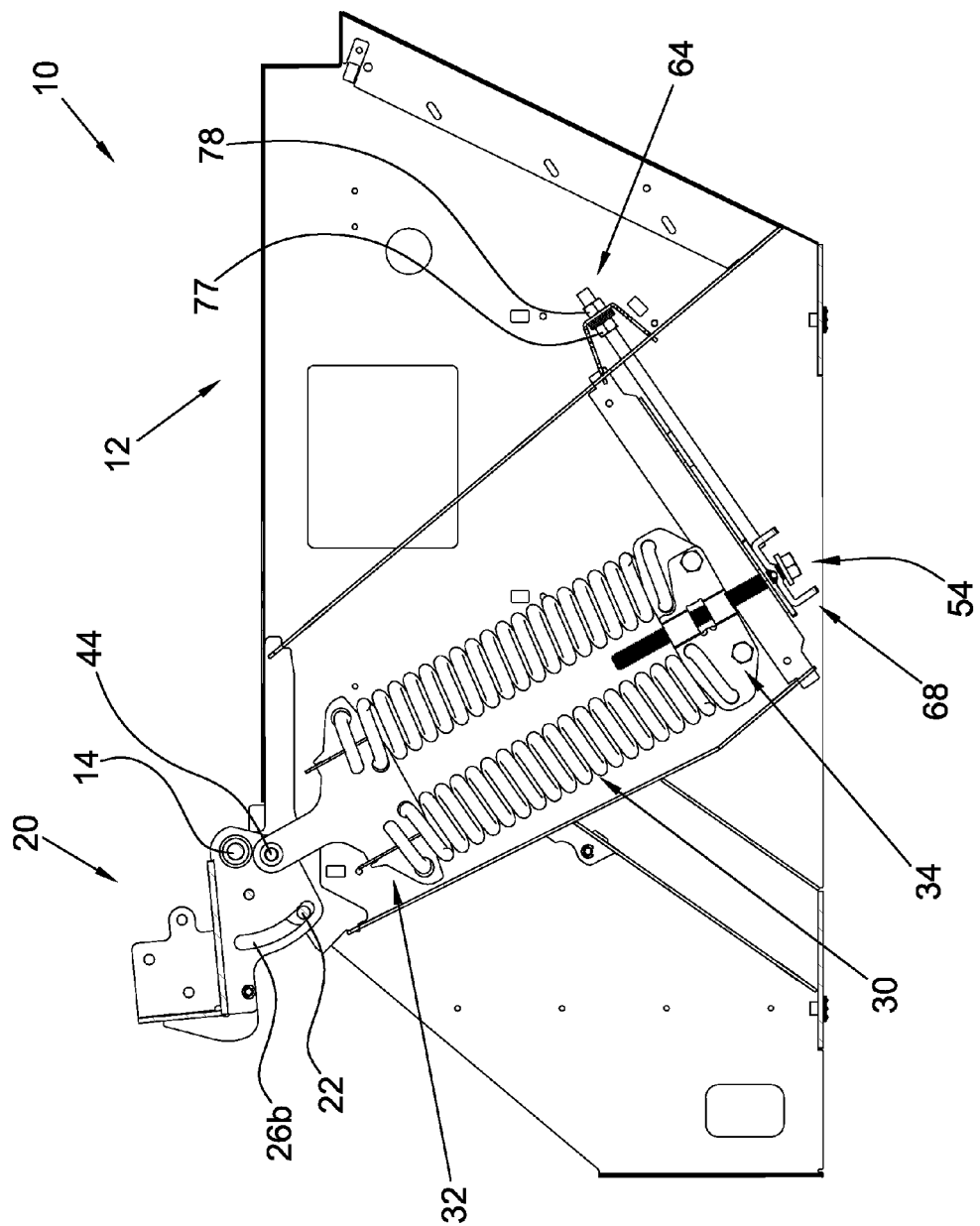
FIG. 9 is a side elevational view of the embodiment of the present invention counterbalance mechanism of FIG. 1 having side walls removed to expose the inner components and having the pivot slider positioned in a rear position.
Figure 10:
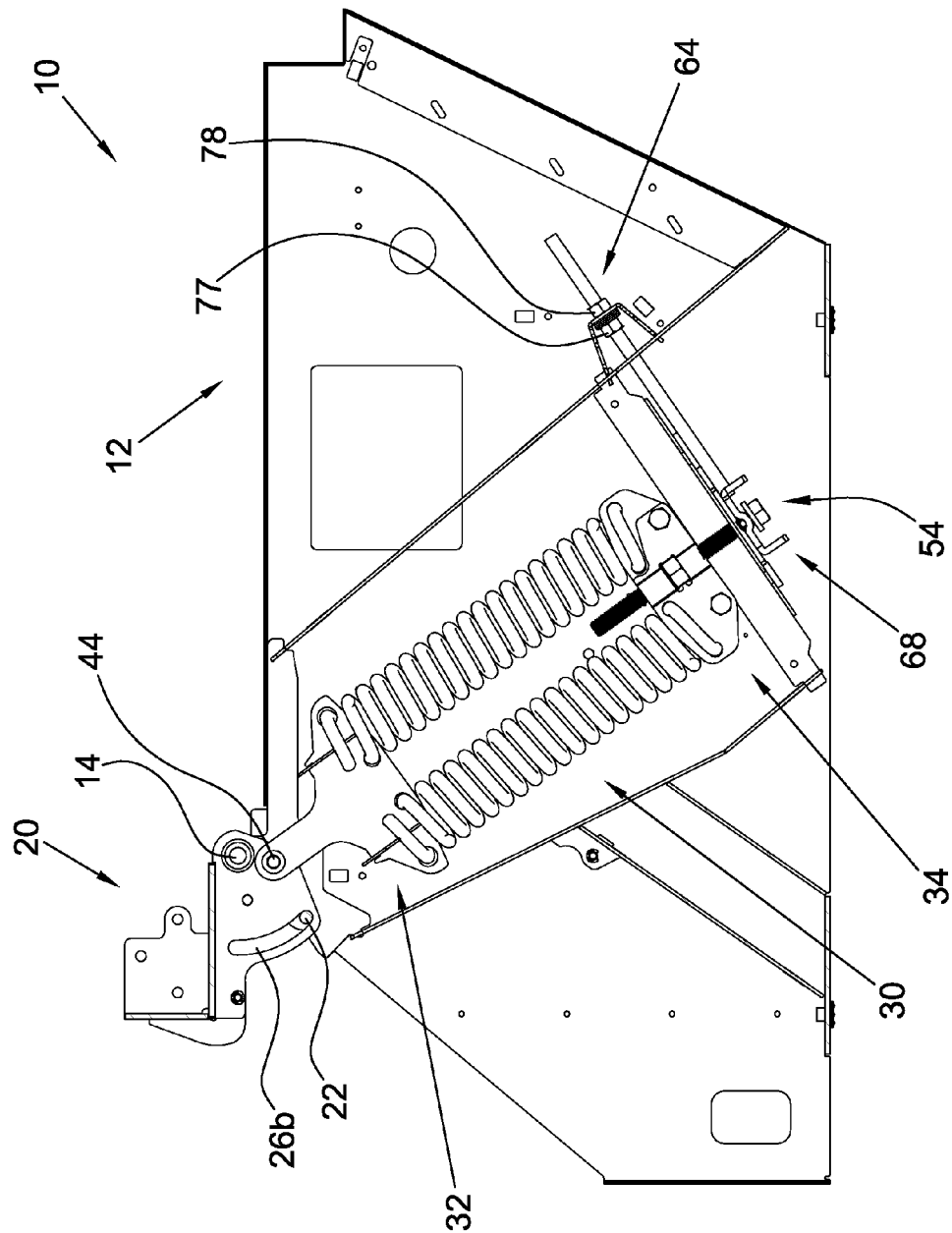
FIG. 10 is a side elevational view of the embodiment of the present invention counterbalance mechanism of FIG. 1 having side walls removed to expose the inner components and having the pivot slider positioned in a forward position.
Figure 11:
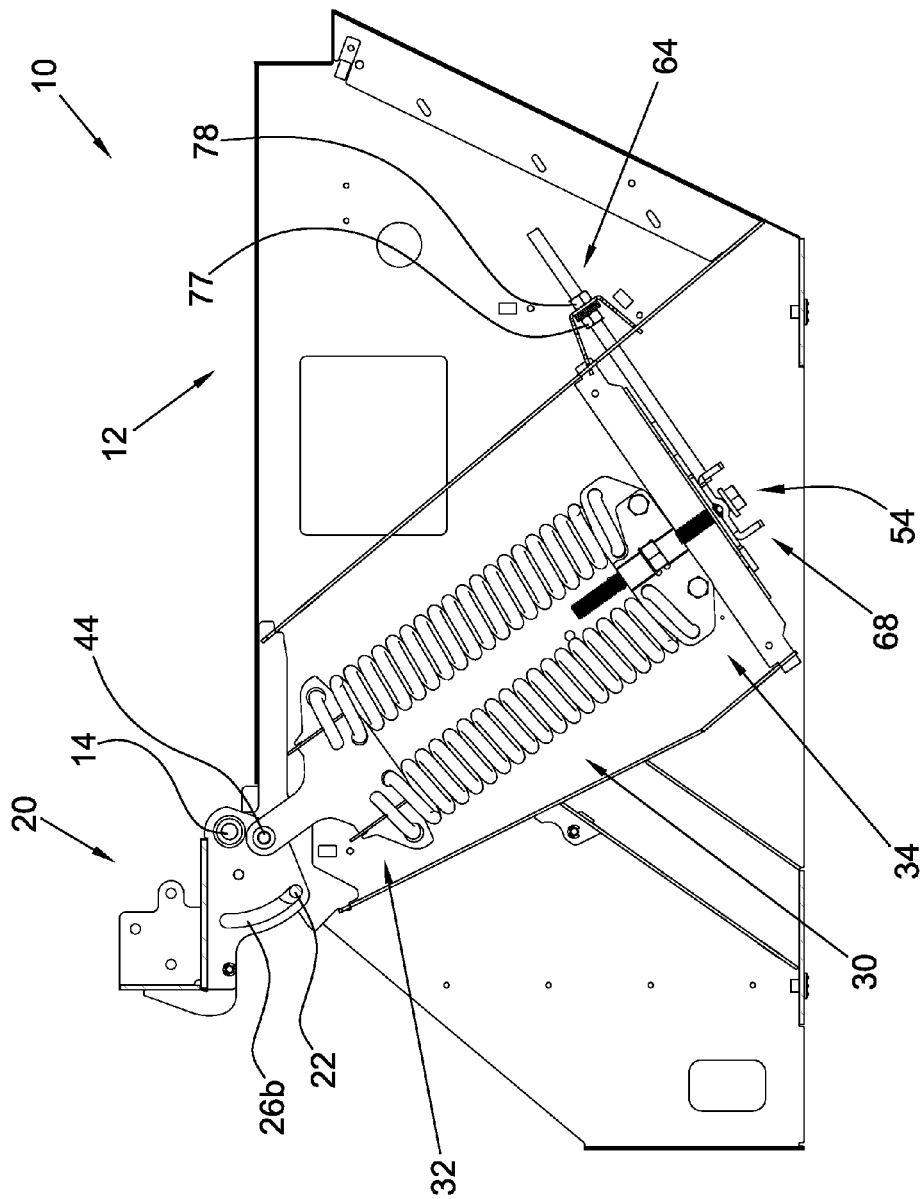
FIG. 11 is a side elevational view of the embodiment of the present invention counterbalance mechanism of FIG. 1 having side walls removed to expose the inner components, having the pivot slider positioned in a middle position and having the pivot nose rotated to a closed position.
Figure 12:
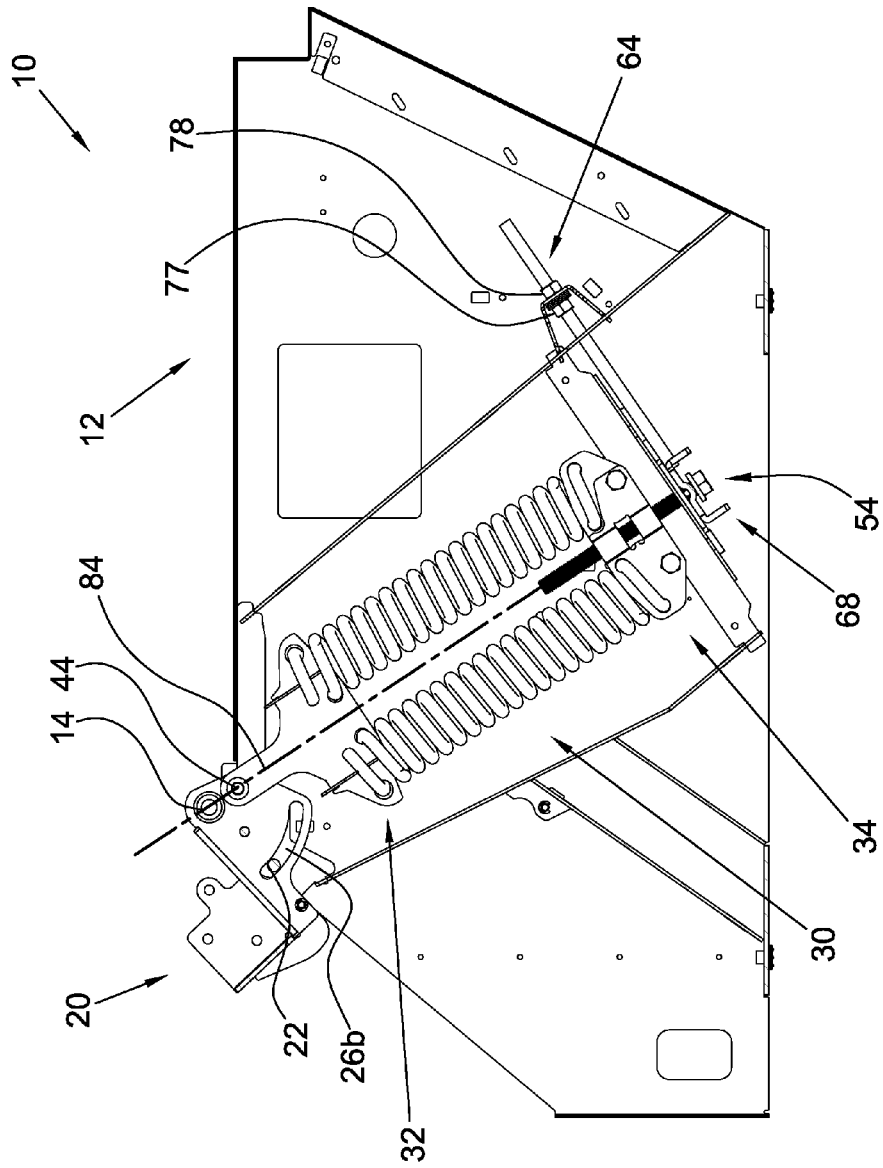
FIG. 12 is a side elevational view of the embodiment of the present invention counterbalance mechanism of FIG. 1 having side walls removed to expose the inner components, having the pivot slider positioned in a middle position and having the pivot nose rotated to a balanced position, i.e., a position where the pivot nose experiences no torque.
Figure 13:
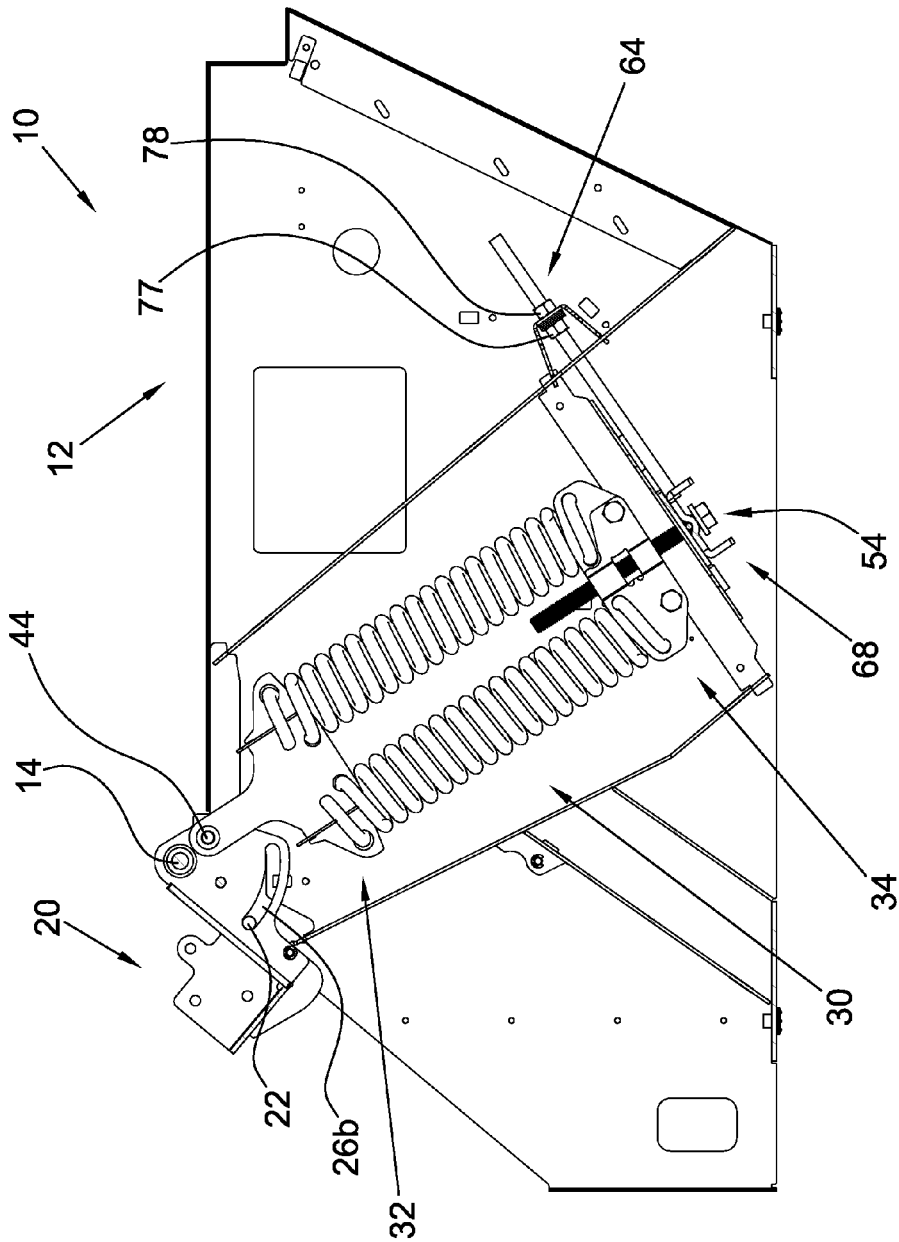
FIG. 13 is a side elevational view of the embodiment of the present invention counterbalance mechanism of FIG. 1 having side walls removed to expose the inner components, having the pivot slider positioned in a middle position and having the pivot nose rotated to an open position.
Figure 14:
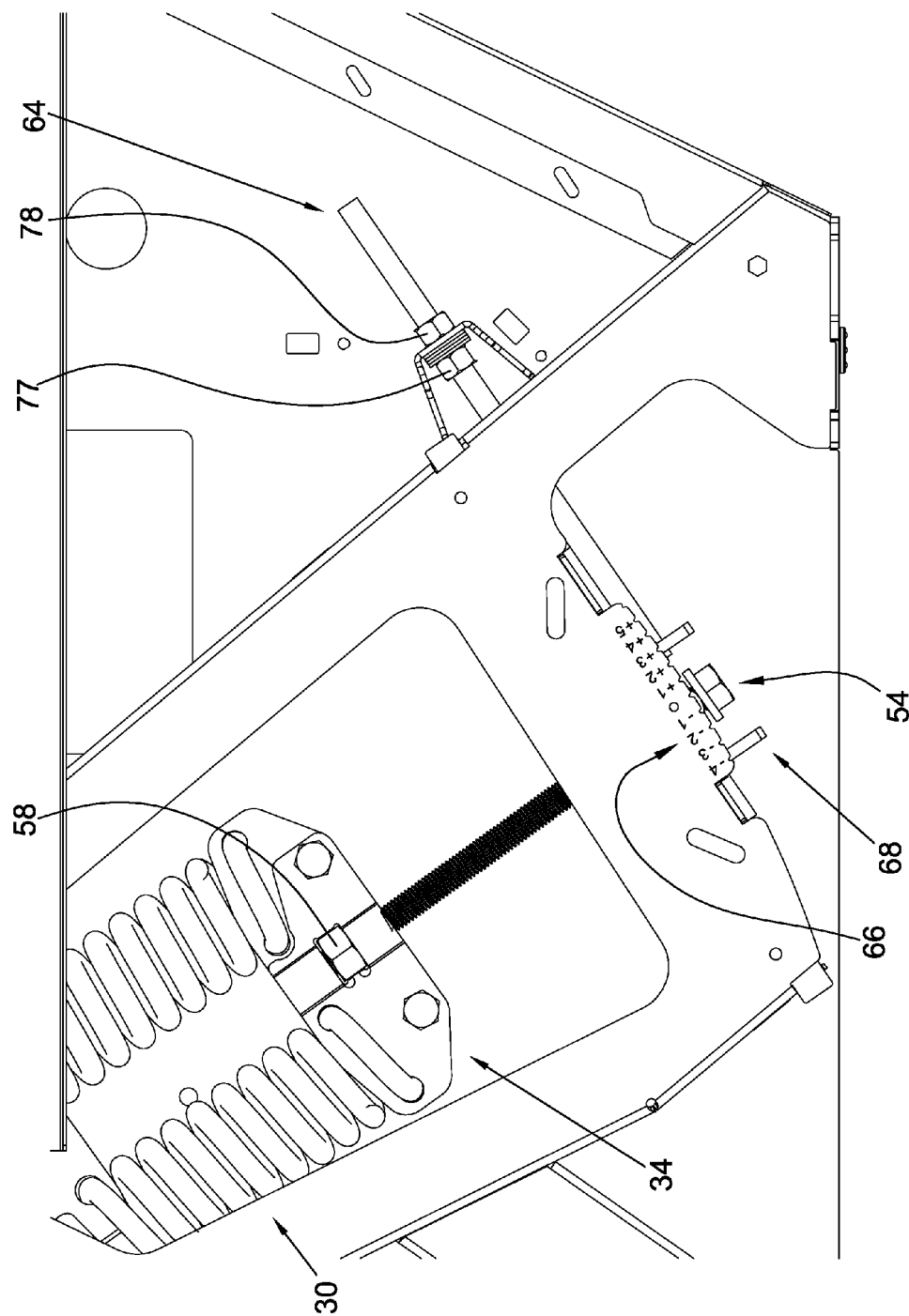
FIG. 14 is an enlarged side elevational view of the embodiment of the present invention counterbalance mechanism of FIG. 1 showing the encircled region A of FIG. 3.

In view of the attachment of pivot slider 62 to second spring mount 34 via force magnitude adjuster 54, as second spring mount 34 is moved in a positive or negative direction in accordance with the scale shown in FIG. 14, the direction of axes 82a and 82b is changed relative to pivot nose 20. FIG. 10 depicts second spring mount 34 in a positive direction, while FIG. 9 depicts second spring mount 34 in a negative direction. Such variation in the direction of axes 82a and 82b results in a change in the force angle of the energy storage device and thereby the rotational position of pivot nose 20 where all forces are balanced, or in other words, the rotational position of pivot nose 20 where the force urging clockwise rotational movement of an object attached to pivot nose 20, e.g., the cover of a tanning bed, is equal to the force urging counterclockwise rotational movement of the object. It should be appreciated that the rotational position of pivot nose 20 where all forces are balanced may also be determined by the relationship of the positions of openings 18a and 18b, openings 48a and 48b, and through hole 72. More specifically, when openings 18a and 18b, openings 48a and 48b, and through hole 72 are in registered alignment, i.e., form a straight line, e.g., line 84 (See FIG. 12), pivot nose 20 experiences no torque. This alignment is calibrated by altering the location of pivot slider 62 as described above.

A further embodiment of a pivot nose assembly for use in the present invention is depicted in FIG. 15. Pivot nose assembly 100 comprises pivot nose 102 which comprises aligned pair of through holes 104a and 104b (not shown), aligned pair of arcuate slots 106a and 106b (not shown), aligned pair of arcuate slots 108a and 108b (not shown) and arcuate slot 110. It should be appreciated that pivot nose 102 includes symmetrical features on each side; however, only one side of pivot nose 102 is shown in FIG. 15. Pivot nose assembly 100 further comprises adjustment plate 112 rotatably secured to pivot nose 102. Adjustment plate 112 is generally U-shaped and is arranged within pivot nose 102. Moreover, adjustment plate 112 is arranged to rotate about aligned pair of through holes 104a and 104b. Adjustment plate 112 comprises aligned pair of arcuate slots 114a and 114b (not shown), through hole 116 and aligned pair of through holes 118a and 118b (not shown), wherein arcuate slots 114a and 114b are arranged adjacent to aligned pair of arcuate slots 106a and 106b, through hole 116 is arranged adjacent to arcuate slot 110 and through holes 118a and 118b is adjacent to aligned pair of arcuate slots 108a and 108b. Rotating adjustment plate 112 relative to pivot nose 102 changes the force direction or force angle of the energy storage device by altering the position of the pivot axis of the energy storage device relative to the pivot axis of pivot nose assembly 100. In other words, rotating adjustment plate 112 about through holes 104a and 104b results in a different position of through holes 118a and 118b, i.e., a different position for the pivot axis of the energy storage device, which in some embodiments is the upper spring mount, e.g., spring mount 32. By altering the position of the energy storage device pivot axis, the relationship between the pivot axis of pivot nose 100 and energy storage device pivot axis is changed thereby resulting in a different force direction or force angle of the energy storage device. It should be appreciated that the rotation of adjustment plate 112 always leaves the same length of arcuate slots 106a and 106b available for travel of a pin or stop therein, in other words, arcuate slots 114a and 114b are arranged to provide clearance for arcuate slots 106a and 106b through all positions of adjustment plate 112. The rotation of adjustment plate 112 may be fixed relative to pivot nose 102 by securing a locking device, e.g., a nut and a bolt, within through hole 116 and arcuate slot 110. It should be appreciated that when using pivot nose assembly 100 in a present invention counterbalance mechanism, it is unnecessary to include the pivot slider assembly, e.g., the lower spring mount, or in other words, spring mount 34 may be fixed. As in the previous embodiments, the aligned registration of the pivot axis of the pivot nose assembly, pivot axis of the energy storage device and the force direction results in substantially no torque applied to the pivot nose.

A further embodiment of an energy storage device for use in a present invention counterbalance mechanism is shown in FIG. 16. Energy storage device 150 comprises tension spring 152. Spring 152 comprises a hook portion disposed at each end of spring 152, i.e., hook portions 154 and 156. In this embodiment, spring mounts are unnecessary. Hook portion 154 rotatably couples spring 152 to spring load pin 44, while hook portion 156 couples spring 152 to force magnitude adjuster 158. Force magnitude adjuster 158 is depicted as a tensioner comprising eyebolt 160 and nut 162. As with the embodiments comprising force magnitude adjuster 54, force magnitude adjuster 158 passes through spanner plate 60 and pivot slider 62.

In view of the foregoing it should be appreciated that pulling the force angle forward, i.e., adjusting the force angle in a positive direction, increases the lift for all lid positions. Moreover, the force angle adjustment is the primary driver to the coast-open or sag near the balance point and open position, while the force magnitude setting is the primary driver to control the lift near the closed position. The two adjustments are related and affect each other, so an iterative adjustment technique results in the optimum counterbalance performance. Having such an arrangement, the present invention counterbalance provides approximately 4000 lbs of spring force, thereby permitting a 300-350 lbs lid/cover to be moved with only 5-10 lbs of force.

Furthermore, some configurations of the present invention counterbalance mechanism may result in an arrangement where a zero torque position is never reached. In such configurations, a lifting torque is always present, or in other words, the greatest torque is provided when the pivot nose is in a closed position and the torque decreases as the pivot nose approaches an open position; however, a zero torque position is never reached. For arrangements of the present invention having a zero torque position, torque is provided in an opening direction for pivot nose positions between the closed position and the zero torque position, while contrarily, torque is provided in a closing direction for pivot nose positions between the open position and the zero torque position.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What we claim is:

1. A counterbalance mechanism comprising:
   a housing comprising a first aligned pair of through holes and a second aligned pair of through holes;
   a pivot nose comprising a third aligned pair of through holes, a fourth aligned pair of through holes and an aligned pair of arcuate slots;
   an energy storage device comprising first and second spring mounts and at least one spring, the first spring mount comprising at least one first flange and a pivot flange having a fifth through hole, the second spring mount comprising at least one second flange and a sixth through hole and the at least one spring comprises first and second ends, the first end is secured to the at least one first flange and the second end is secured to the at least one second flange;
   a first pivot pin disposed in the first aligned pair of through holes and the third aligned pair of through holes;
   a stop member disposed in the second aligned pair of through holes and the aligned pair of arcuate slots;
   a second pivot pin disposed in the fourth aligned pair of through holes and the fifth through hole;
   a force magnitude adjuster arranged to control a force of the at least one spring; and,
   a force angle adjuster arranged to control a force direction of the at least one spring.

2. The counterbalance mechanism of claim 1 wherein the housing comprises a seventh through hole and the force angle adjuster is arranged to pass through the seventh through hole.

3. The counterbalance mechanism of claim 1 wherein the fourth aligned pair of through holes are keyed through holes.

4. The counterbalance mechanism of claim 1 wherein the first spring mount comprises a pair of oppositely disposed first flanges arranged symmetrically about the pivot flange, the second spring mount comprises a pair of oppositely disposed second flanges arranged symmetrically about the sixth through hole and two springs each comprising first and second ends, each of the first ends is secured to one of the pair of first flanges and each of the second ends is secured to one of the pair of second flanges.

5. The counterbalance mechanism of claim 1 wherein the force magnitude adjuster controls the force of the at least one spring by altering a length of the at least one spring.

6. The counterbalance mechanism of claim 1 wherein the force angle adjuster controls the force direction by altering a position of the second spring mount relative to the fifth through hole.

7. The counterbalance mechanism of claim 1 wherein the stop member is a third pivot pin.

8. The counterbalance mechanism of claim 1 wherein aligned registration of the first pivot pin, the second pivot pin and the force direction results in substantially no torque applied to the pivot nose.

9. A counterbalance mechanism comprising: a housing comprising a first aligned pair of through holes and a second aligned pair of through holes; a pivot nose comprising a third aligned pair of through holes, a fourth aligned pair of through holes and an aligned pair of arcuate slots; an energy storage device comprising a first end and a second end opposite the first end, the energy storage device selected from the group consisting of: a spring and a pressure cylinder; a first pivot pin disposed in the first aligned pair of through holes and the third aligned pair of through holes; a stop member disposed in the second aligned pair of through holes and the aligned pair of arcuate slots; a second pivot pin disposed in the fourth aligned pair of through holes and pivotally connected to the energy storage device adjacent the first end; a force magnitude adjuster arranged to control a force of the energy storage device; and, a force angle adjuster arranged to control a force direction of the energy storage device, wherein the force magnitude adjuster and force angle adjuster are positioned adjacent the second end of the energy storage device.

* * * * *